US00PP27640P3

(12) United States Plant Patent
Trees

(10) Patent No.: US PP27,640 P3
(45) Date of Patent: Feb. 7, 2017

(54) ROSA PLANT NAMED 'SFROSA128'

(50) Latin Name: *Rosa hybrida*
Varietal Denomination: SFROSA128

(71) Applicant: Scott Trees, Arroyo Grande, CA (US)

(72) Inventor: Scott Trees, Arroyo Grande, CA (US)

(73) Assignee: Sunrise Farm Flowers, LLC, Arroyo Grande, CA (US)

( * ) Notice: Subject to any disclaimer, the term of this patent is extended or adjusted under 35 U.S.C. 154(b) by 0 days.

(21) Appl. No.: 14/756,578

(22) Filed: Sep. 18, 2015

(65) Prior Publication Data

US 2016/0295758 P1 Oct. 6, 2016

Related U.S. Application Data

(60) Provisional application No. 62/178,086, filed on Mar. 31, 2015.

(51) Int. Cl.
*A01H 5/02* (2006.01)

(52) U.S. Cl.
USPC ..... Plt./104

(58) Field of Classification Search
USPC ..... Plt./104
CPC ..... A01H 5/0222
See application file for complete search history.

*Primary Examiner* — Kent L Bell
(74) *Attorney, Agent, or Firm* — Audrey Charles

(57) ABSTRACT

A new and distinct cultivar of shrub rose plant named 'SFROSA128', characterized by its semi-double type, bright yellow-colored flowers, medium to light green-colored foliage, and moderately vigorous, compact, upright-mounded growth habit, is disclosed.

1 Drawing Sheet

Latin name of genus and species of plant claimed: *Rosa hybrida.*

Variety denomination: 'SFROSA128'.

BACKGROUND OF THE INVENTION

The present invention relates to a new and distinct cultivar of *Rosa hybrida*. The new cultivar will be referred to hereafter by its cultivar name, 'SFROSA128'. 'SFROSA128' is a new cultivar of shrub rose grown for use as a landscape shrub.

The new cultivar originated in a controlled breeding program in Arroyo Grande, Calif. during July 2009. The objective of the breeding program was to create new shrub rose cultivars with disease resistance, ever blooming habits, unique brightly colored flowers that can be readily propagated on their own roots.

The new shrub rose cultivar is the result of open-pollination. The female (seed) parent of the new cultivar is 'Sun Flare', not patented, characterized by its semi-double type, medium yellow-colored flowers, dark green-colored foliage, low growth vigor and compact-mounded growth habit. The male (pollen) parent of the new cultivar is unknown. The new cultivar was discovered and selected as a single flowering plant within the progeny of the above stated open-pollination during October 2010 in a controlled environment in Arroyo Grande, Calif.

Asexual reproduction of the new cultivar by stem cuttings since October 2010 in Arroyo Grande, Calif. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'SFROSA128' as a new and distinct cultivar of shrub rose plant:

1. Semi-double type, bright yellow-colored flowers;
2. Medium to light green-colored foliage; and
3. Moderately vigorous, compact, upright-mounded growth habit.

Plants of the new cultivar differ from plants of the female parent primarily in having lighter green foliage, smaller flowers, and a more upright growth habit.

Of the many commercially available shrub rose cultivars, the most similar in comparison to the new cultivar is 'Sunsprite', U.S. Plant Pat. No. 3,509, expired. However, in side by side comparisons, plants of the new cultivar differ from plants of 'Sunsprite' in at least the following characteristics:

1. Plants of the new cultivar have fewer petals than plants of 'Sunsprite';
2. Plants of the new cultivar repeat bloom faster than plants of 'Sunsprite'; and
3. Plants of the new cultivar have petal edges that curl backwards more than plants of 'Sunsprite'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'SFROSA128'. The plants were approximately two-years old and grown in in the ground in West Chicago, Ill. for approximately three months.

DETAILED BOTANICAL DESCRIPTION

Figure 1:
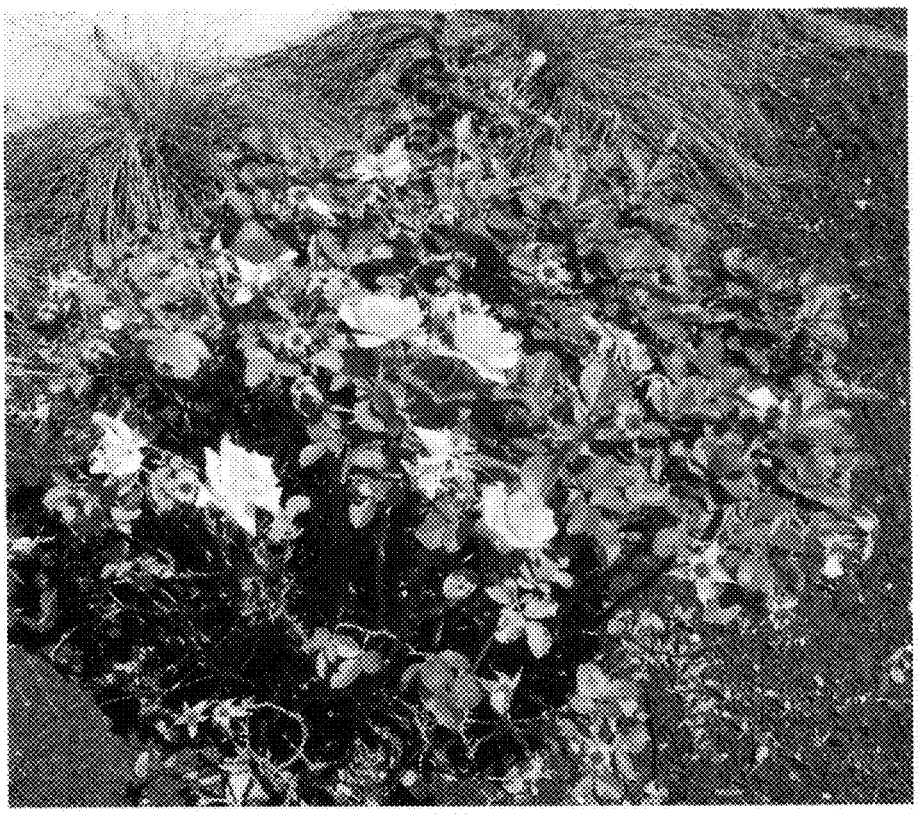
FIG. 1 illustrates a side view of the overall growth and flowering habit of 'SFROSA128'.
Figure 2:
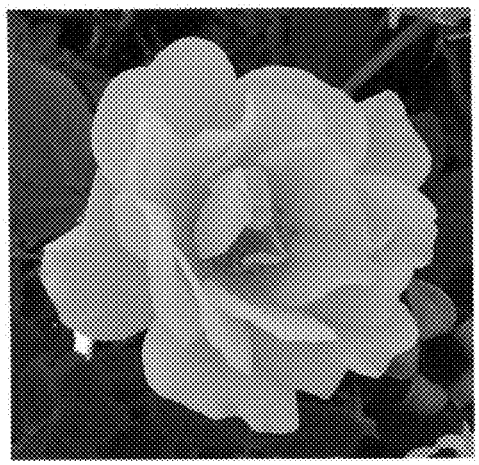
FIG. 2 illustrates a close-up view of an individual flower of 'SFROSA128'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in July 2015 under natural light conditions in West Chicago, Ill.

The following is a detailed description of plants that were approximately two-years old. Plants were grown in in the ground in West Chicago, Ill. under garden-like conditions for approximately three months. Measurements and numerical values represent averages of typical plants.

Botanical classification: *Rosa hybrida* cultivar SFROSA128.

Parentage:

*Female parent.*—'Sun Flare', not patented.

*Male parent.*—Unknown.

Propagation:

*Type cutting.*—Stem.

*Time to initiate roots.*—Approximately 14 to 21 days.

*Time to produce a rooted cutting.*—Approximately 30 to 45 days.

*Root description.*—Fibrous.

*Rooting habit.*—Freely branching.

Plant description:

*Plant type.*—Deciduous shrub.

*Cold hardiness.*—At least to USDA Zone 5.

*Diseases and pests.*—Has shown tolerance to be resistant to powdery mildew and rust.

*Commercial crop time.*—Approximately 12 to 15 weeks from a rooted cutting to finish in a one-gallon container.

*Growth rate and habit.*—Moderately vigorous, compact, upright-mounded.

*Size.*—Height from soil level to top of plant plane: Approximately 60.0 cm. Width: Approximately 70.0 cm.

*Branching habit.*—Freely branching. Quantity of primary stems per plant: Approximately 6. Quantity of lateral branches per primary stem: Approximately 2 to 4.

*Lateral branch.*—Strength: Strong. Length: Approximately 28.0 cm. Diameter: Approximately 6.0 mm. Length of central internode: Approximately 2.5 cm. Texture: Glabrous with thorns. Color of young branch: 144A, glaucous. Color of mature branch: Closest to but darker than 144A, with age becomes woody N199B.

*Thorns.*—Shape: Triangular, with oval base and sharp pointed apices. Aspect: Pointed downward. Density: Approximately 1 to 2 per linear centimeter. Length: Approximately 9.0 mm. Diameter at midpoint: Approximately 1.0 mm. Texture: Glabrous. Color: 145B maturing to 165B.

Foliage description:

*General description.*—Form: Compound, division is odd-pinnate, 5 to 7 leaflets. Fragrance: None detected. Aspect: Typically perpendicular to stem. Arrangement: Alternate. Overall shape: Elliptic. Length of mature leaf: Approximately 7.5 cm. Width of mature leaf: Approximately 5.5 cm.

*Leaflets.*—Shape: Elliptic. Margin: Serrulate. Apex: Cuspidate. Base: Obtuse. Venation pattern: Pinnate. Terminal leaflet length: Approximately 3.0 cm. Terminal leaflet width: Approximately 2.5 cm. Lateral leaflet length: Approximately 2.8 cm. Lateral leaflet width: Approximately 2.0 cm. Texture of upper and lower surfaces: Glabrous. Color of upper surface of young foliage: Closest to but darker green than 144A with venation of 144A. Color of lower surface of young foliage: 146D with venation of 145A. Color of upper surface of mature foliage: N137D with venation of 144A. Color of lower surface of mature foliage: Closest to 146C with venation of 146D. Length of rachis: Approximately 3.0 cm. Diameter of rachis: Approximately 1.0 mm. Texture of upper and lower surfaces of rachis: Sparsely pubescent. Color of upper and lower surfaces of rachis: 144A.

*Petiole.*—Length: Approximately 2.0 cm. Diameter: Approximately 1.0 mm. Texture: Sparsely pubescent. Color: 144A.

*Petiolules.*—Length: Approximately 1.0 mm. Diameter: Approximately 1.0 mm. Texture: Glabrous. Color: 144A.

*Stipules.*—Quantity: 2 per leaf. Aspect: Adnate to petiole with free apex outwardly pointed. Shape: Acute. Margin: Entire, ciliate. Length: Approximately 9.0 mm and a free apex portion of approximately 4.0 mm. Width: Approximately 1.0 mm. Texture: Glabrous. Color: 144A.

Flowering description:

*Flowering habit.*—Continuous bloom in California and from June to first frost in the Midwestern, northeastern, and southeastern areas of the United States.

*Lastingness of individual inflorescence on the plant.*—Approximately 5 to 8 days depending on temperature and sunlight exposure.

Flower description:

*General description.*—Type: Semi-double. Form: Rosette, solitary at terminus and upper nodes of lateral branches. Aspect: Facing upward and outward. Quantity per plant: Approximately 8. Fragrance: Mild tea scent. Diameter: Approximately 9.0 cm. Depth: Approximately 4.0 cm.

*Bud.*—Quantity per plant: Approximately 5. Shape: Ovoid. Length: Approximately 3.0 cm. Diameter: Approximately 1.2 cm. Texture: Sparsely pubescent. Color: Calyx 144A, petals 12A.

*Petals.*—Quantity: 20 (including 1 to 3 petaloids), drop readily and cleanly. Arrangement: Imbricate whorls. Shape: Obcordate to obovate. Margin: Entire, edges curl backwards. Apex: Obcordate to rounded. Base: Attentuate. Length of outermost: Approximately 5.0 cm. Width of outermost: Approximately 5.0 cm. Length of innermost: Approximately 4.0 cm. Width of innermost: Approximately 3.5 cm. Texture of upper and lower surfaces: Glabrous. Color of upper surface when first open: 12A. Color of lower surface when first open: 12B. Color of upper surface when fully open: 4C with base of 4A. Color of lower surface when fully open: 4D with base of 4B.

*Calyx.*—Shape: Star-like, highly reflexed. Diameter: Approximately 2.4 cm. Depth: Approximately 3.5 cm.

*Sepals.*—Quantity per flower: 5, fused at base. Shape: Lanceolate. Apex: Acute, caudate. Length: Approximately 3.7 cm. Width at base: Approximately 8.0 mm. Texture of upper (inner) surface: Tomentose. Texture of lower (outer) surface: Glabrous. Color of upper (inner) surface: 138B, appears lighter due to pubescence. Color of lower (outer) surface: 144A.

*Peduncle.*—Strength: Strong. Aspect: Erect. Length: Approximately 2.0 cm. Diameter: Approximately 3.0 mm. Texture: Glabrous with immature thorns. Color: Closest to 144A.

*Hypanthium.*—Shape: Cup-like. Length: Approximately 1.0 cm. Diameter: Approximately 1.0 cm. Texture: Sparsely pubescent. Color: Closest to 144B.

*Reproductive organs.*—Androecium: Stamen quantity: Approximately 140. Stamen length: Approximately 1.2 cm. Filament length: Approximately 1.0 cm. Filament color: Close to 151 D. Anther shape: Reniform. Anther length: Approximately 2.0 mm to 3.0 mm. Anther color: Close to 151D with 23B. Pollen amount: Sparse. Pollen color: 23A. Gynoecium: Appearance: Ovaries and lower portion of styles embedded in hypanthium, numerous long white hairs attached to base and apex of ovaries. Pistil quantity: Approximately 70. Pistil length: Approximately 1.4 cm. Stigma shape: Bi-lobed. Stigma length: Approximately 1.0 mm. Stigma color: 4C. Style length: Approximately 1.0 cm. Style color: 145D. Ovary length: Approximately 3.0 mm. Ovary color: 155A.

*Hips.*—Not observed, plant is highly sterile.

What is claimed is:

1. A new and distinct cultivar of shrub rose plant named 'SFROSA128', substantially as herein illustrated and described.

* * * * *